(12) United States Patent
Kim, I et al.

(10) Patent No.: US 9,446,081 B2
(45) Date of Patent: Sep. 20, 2016

(54) PHARMACEUTICAL COMPOSITION FOR PREVENTING AND TREATING COMPLICATIONS OF DIABETES CONTAINING A TRADITIONAL ORIENTAL MEDICINE EXTRACT OR A FRACTION THEREOF AS AN ACTIVE INGREDIENT

(75) Inventors: Jin Sook Kim, I, Seoul (KR); Jung Hyun Kim, Seoul (KR); Young Sook Kim, Daejeon (KR); Chan-Sik Kim, Daejeon (KR); Ohn Soon Kim, Daejeon (KR); Eun Jin Shon, Daejeon (KR); Nam-Hee Yoo, Daejeon (KR); Yun Mi Lee, Daejeon (KR); Dong Ho Jung, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 13/983,802

(22) PCT Filed: Mar. 7, 2011

(86) PCT No.: PCT/KR2011/000896
§ 371 (c)(1),
(2), (4) Date: Aug. 6, 2013

(87) PCT Pub. No.: WO2012/121423
PCT Pub. Date: Sep. 13, 2012

(65) Prior Publication Data
US 2013/0316030 A1    Nov. 28, 2013

(51) Int. Cl.
| | |
|---|---|
| *A61K 36/47* | (2006.01) |
| *A61K 36/00* | (2006.01) |
| *A23L 1/30* | (2006.01) |
| *A23L 1/314* | (2006.01) |
| *A23L 1/39* | (2006.01) |
| *A23L 2/52* | (2006.01) |
| *A23K 1/16* | (2006.01) |
| *A23K 1/18* | (2006.01) |

(52) U.S. Cl.
CPC .............. *A61K 36/00* (2013.01); *A23K 1/1646* (2013.01); *A23K 1/184* (2013.01); *A23K 1/1813* (2013.01); *A23K 1/1826* (2013.01); *A23L 1/3002* (2013.01); *A23L 1/31436* (2013.01); *A23L 1/39* (2013.01); *A23L 2/52* (2013.01); *A61K 36/47* (2013.01); *A23C 2240/15* (2013.01)

(58) Field of Classification Search
CPC ............................. A61K 36/00; A61K 36/47
USPC ................................................ 424/725, 731
See application file for complete search history.

(56) References Cited

FOREIGN PATENT DOCUMENTS

| | | | |
|---|---|---|---|
| CN | 101032545 A | * | 9/2007 |
| JP | 2004-182712 A | | 7/2004 |
| KR | 1020110058156 A | | 8/2011 |

OTHER PUBLICATIONS

Navarro et al. "Role of inflammation in diabetic complications" Nephrol Dial Transplant (2005) 20:2601-2604.*
Hovind et al "Serum Uric Acid as a Predictor for Development of Diabetic Nephropathy in Type 1 Diabetes", Diabetes, vol. 58, Jul. 2009.*
Shu-min Yang et al; Chemical Constituents From the Roots of Homonoia Riparia; Acta Pharmaceutica Sinica, 2007, pp. 292-296.

* cited by examiner

*Primary Examiner* — Chris R Tate
*Assistant Examiner* — Deborah Davis
(74) *Attorney, Agent, or Firm* — Norton Rose Fulbright US LLP

(57) ABSTRACT

The present invention relates to a pharmaceutical composition for the prevention and treatment of diabetic complications comprising the extract of *Homonoia riparia* Lour. or the fraction thereof as an active ingredient. More particularly, the extract of *Homonoia riparia* Lour. or the fractions thereof of the present invention can inhibit the activity of aldose reductase and the generation of the advanced glycation endproducts, the index of diabetic complications, and have powerful activity of inhibiting diabetic complications with brining the anti-cataract, anti-retinopathy, and anti-neuropathy effect, and have the activity of anti-oxidation as well, so that they can be effectively used as an active ingredient of a pharmaceutical composition for the prevention and treatment of diabetic complications.

5 Claims, 10 Drawing Sheets

PHARMACEUTICAL COMPOSITION FOR PREVENTING AND TREATING COMPLICATIONS OF DIABETES CONTAINING A TRADITIONAL ORIENTAL MEDICINE EXTRACT OR A FRACTION THEREOF AS AN ACTIVE INGREDIENT

CROSS-REFERENCE TO RELATED APPLICATIONS

This application is a 371 of PCT/KR2011/000896, filed Mar. 7, 2011, the contents of which are incorporated herein by reference.

BACKGROUND OF THE INVENTION

1. Field of the Invention

The present invention relates to a pharmaceutical composition for the prevention and treatment of diabetic complications comprising the extract of *Homonoia riparia* Lour. or the fraction thereof as an active ingredient.

2. Description of the Related Art

Diabetes mellitus is one of the important adult diseases that concerns us world-widely. Along with the rapid industrial breakthrough, prevalence rate of diabetes reaches 10% recently in Korea and the total diabetes patients in the world are estimated to be at least 240 million, which will be growing to approximately 380 million in 2025.60% of them will be developed in Asia, according to the 2009 report of JAMA. In particular, considering that the diabetes on-set period has been brought forward to middle-aged group and human life-span has been prolonged, it seems hard to avoid many cases of diabetic complications. That is, diabetic complications such as diabetic retinopathy, diabetic cataract, diabetic nephropathy, diabetic neuropathy, heart disease, cancer and osteoporosis are observed generally 10~20 years after diabetes is taken, during which almost every organ in human body is going to be damaged. Chronic diabetic nephropathy is the major reason of hemodialysis treatment and end-stage renal disease. Diabetic cataract and diabetic retinopathy can cause blindness and even death. The reason of blindness in the age of 25~74 is diabetes in USA. 60% of diabetes patients experience blindness 15~20 years after taking diabetes. Therefore, if diabetic complications can be delayed at least 5~10 years, the quality of life of diabetes patients and their family can be greatly enhanced, which can also be advantageous to national finance.

The mechanism that can cause diabetic complications is explained by nonenzymatic glycation of protein, polyol pathway, and oxidative stress, etc. Nonenzymatic glycation of protein is induced by Maillad reaction, the nonenzymatic condensation of amino acid group such as lysine residue and reducing sugar. Advanced glycation endproducts (AGEs) are produced by this reaction. More particularly, nonenzymatic glycation of protein is carried out by the following steps: (1) amino acid group such as lysine residue and aldehyde or ketone of reducing sugar form the primary product, schiff base, via nonenzymatic nucleophilic addition reaction, and then the produced schiff base is condensated with neighboring ketoamine adduct to produce reversible Amadori type glycation products; and (2) the reversible Amadori type glycation products are not decomposed but rearranged to produce irreversible advanced glycation endproducts under hyperglycemic state, and the produced advanced glycation endproducts are bound to protein or lipid by cross-linking to produce irreversible glycated protein or glycated lipid. Unlike the reversible Amadori type early glycation products, the advanced glycation endproducts are irreversible, indicating that once the advanced glycation endproducts are produced they are not converted even when blood sugar level goes back to normal and instead they are accumulated in tissues as long as the protein or lipid to which the products are conjugated lives to cause abnormal changes in the structures and functions of many tissues, resulting in the complications (Vinson, J. A. et al., 1996, *J. Nutritinal Biochemistry* 7: 559-663; Smith, P. R. et al., 1992, *Eur. J. Biochem.*, 210: 729-739). For example, glycated albumin, one of the advanced glycation endproducts produced by the reaction of many kinds of protein and glucose, is a critical reason of chronic diabetic nephropathy. Glycated albumin flows more easily into renal glomerular cells than non-glycated normal albumin, and glucose at high concentration stimulates mesangium cells to increase extracellular matrix synthesis. The excessively influxed glycated albumin and the increased extracellular matrix cause fibrosis of renal glomerulus. Renal glomerulus is continuously damaged by such mechanism, requiring extreme treatment methods such as hemodialysis or organ transplantation. According to the previous reports, as diabetes continues collagen is accumulated as being conjugated with the advanced glycation endproducts in arterial wall and so is basement membrane protein conjugated with the advanced glycation endproducts in renal glomerulus (Brownlee, M., et al., 1986, *Sciences*, 232, 1629-1632). Such nonenzymatic glycation causes a series of glycations in such proteins as basement membrane protein, plasma albumin, lens protein, fibrin and collagen, and then the produced advanced glycation endproducts induce abnormal changes in the structures and functions of various tissues to cause chronic diabetic complications such as diabetic retinopathy, diabetic cataract, diabetic nephropathy, diabetic neuropathy, etc. In the process of the generation of advanced glycation endproducts under hyperglycemic state, lipid metabolism turns into abnormal and toxic oxygen free-radical is generated, resulting in the decrease of defense system and the increase of oxidative stress (Yokozawa, T., et al, 2001, *J. of Trad. Med.*, 18: 107-112). As explained hereinbefore, nonenzymatic glycation is closely related to oxidative stress mechanism.

Polyol pathway is the process comprising the following steps; (1) Aldose or ketose is reduced into sorbitol by the action of aldose reductase (AR); and (2) The produced sorbitol is oxidized by sorbitol dehydrogenase to produce fructose. In normal condition, aldose reductase has a weak affinity to glucose. However in hyperglycemic state, aldose reductase, the first enzyme of polyol pathway, is over-activated and the excessive blood glucose is converted into sorbitol and fructose which are accumulated in tissues with breaking the balance of osmotic pressure to cause complications. Because of the abnormally increased osmotic pressure, water flows in more, which can progress to diabetic retinopathy, diabetic neuropathy, and diabetic cataract, etc. (Kim, et al., Diabetes, Korean Diabetes Association, Korea Medical Book Publishing, 483; Soulis-Liparota, T., et al., 1995, *Diabetologia*, 38: 357-394). According to the previous report, the advanced glycation endproducts activate aldose reductase which is the major enzyme of polyol pathway in human microvascular endothelial cells (Nakamura, N., et al., 2000, *Free Radic Biol. Med.*, 29: 17-25). At this time, nonenzymatic glycation of fructose is 10 times faster than that of glucose. Thus, fructose at high concentration is bound with protein to accelerate the production of the advanced glycation endproducts. So, nonenzymatic glycation, polyol pathway, and oxidative stress mechanism are all connected to cause diabetic complications. In the middle of the generation of the advanced glycation endproducts in hyperglycemic state, abnormal changes occur in lipid metabolism and at the same time toxic oxygen free-radical is generated. Then, defense system against such oxygen free-radical is reduced in the course, so that oxidative stress is induced (Yokozawa, T., et al, 2001, J. of Trad. Med., 18: 107-112). That also confirms the interrelation between nonenzymatic glycation and oxidative stress mechanism. Therefore, to delay or prevent or treat diabetic complications, it is important to inhibit the generation of the advanced glycation endproducts (Brownlee, M., et al., 1988, *N. Engl. Med.,* 318, 1315-1321).

Aminoguanidine, the synthetic protein glycation inhibitor, is nucleophilic hydrazine, which is conjugated with Amadori products to prevent cross linking with protein, by which the generation of the advanced glycation endproducts is inhibited to delay or prevent the progress to diabetic complications (Brownlee, M., et al., 1986, *Sciences,* 232, 1629-1632; Edelstein, D. et al., 1992, *Diabetes,* 41, 26-29). Aminoguanidine is the synthetic medicine which is the most promising agent so far for the prevention and treatment of diabetic complications and is through the phase III clinical test. However, further clinical test has been canceled because of toxicity induced by the long term administration. Thus, it is required to develop a safer and more efficient natural medicine.

*Homonoia riparia* Lour. is evergreen shrub belonging to Euphoribiaceae. The height of *Homonoia riparia* Lour. is 0.5~3 m and flowers come out in January~May. *Homonoia riparia* Lour. is distributed widely in Korea, India, China, Taiwan, and New Guinea, etc. According to Chinese Medicine, it has bitter taste and cold character. It has the medicinal effect of dissipating heat and detoxifying and diuretic effect. However, the pharmacological action and functions of each ingredient of *Homonoia riparia* Lour., particularly the effect on diabetes or diabetic complications, have not been disclosed, yet.

In the middle of research to develop a safer and more efficient natural drug having no toxicity and side effects for the prevention or treatment of diabetic complications, the present inventors confirmed that The extract of *Homonoia riparia* Lour. or the fraction thereof had strong activity of inhibiting diabetic complications by suppressing the generations of the advanced glycation endproducts and aldose reductase, in addition to the activity of preventing aging or anti-cancer activity, leading to the completion of this invention.

SUMMARY OF THE INVENTION

It is an object of the present invention to provide a pharmaceutical composition for the prevention and treatment of diabetic complications comprising the extract of *Homonoia riparia* Lour. or the fraction thereof as an active ingredient.

To achieve the above object, the present invention provides a pharmaceutical composition for the prevention and treatment of diabetic complications comprising the extract of *Homonoia riparia* Lour. or the fraction thereof as an active ingredient.

The present invention also provides a pharmaceutical composition for the prevention and treatment of diabetic complications comprising the fraction obtained from the extract of *Homonoia riparia* Lour. by fractionation using an organic solvent as an active ingredient.

The present invention also provides a health functional food for the prevention and improvement of diabetic complications comprising the extract of *Homonoia riparia* Lour. or the fraction thereof as an active ingredient.

The present invention also provides a functional feed additive for the prevention and improvement of diabetic complications comprising the extract of *Homonoia riparia* Lour. or the fraction thereof as an active ingredient.

The present invention also provides a composition for the inhibition of the advanced glycation endproducts production comprising the extract of *Homonoia riparia* Lour. or the fraction thereof as an active ingredient.

The present invention also provides a pharmaceutical composition for the prevention and delay of aging comprising the extract of *Homonoia riparia* Lour. or the fraction thereof as an active ingredient.

The present invention also provides a health functional food for the prevention and delay of aging comprising the extract of *Homonoia riparia* Lour. or the fraction thereof as an active ingredient.

The present invention also provides a pharmaceutical composition for the prevention and treatment of cancer comprising the extract of *Homonoia riparia* Lour. or the fraction thereof as an active ingredient.

The present invention also provides a health functional food for the prevention and improvement of cancer comprising the extract of *Homonoia riparia* Lour. or the fraction thereof as an active ingredient.

The present invention also provides a method for the prevention or treatment of diabetic complications containing the step of administering a pharmaceutically effective dose of the composition comprising the extract of *Homonoia riparia* Lour. or the fraction thereof as an active ingredient to a subject having diabetic complications.

The present invention also provides a method for inhibiting the production of advanced glycation endproducts containing the step of administering a pharmaceutically effective dose of the composition comprising the extract of *Homonoia riparia* Lour. or the fraction thereof as an active ingredient to a subject.

The present invention also provides a method for inhibiting aging containing the step of administering a pharmaceutically effective dose of the composition comprising the extract of *Homonoia riparia* Lour. or the fraction thereof as an active ingredient to a subject.

The present invention also provides a method for the prevention or treatment of cancer containing the step of administering a pharmaceutically effective dose of the composition comprising the extract of *Homonoia riparia* Lour. or the fraction thereof as an active ingredient to a subject having cancer.

The present invention also provides a use of The extract of *Homonoia riparia* Lour. or the fraction thereof for the production of a pharmaceutical composition for the prevention and treatment of diabetic complications.

The present invention also provides a use of The extract of *Homonoia riparia* Lour. or the fraction thereof for the production of a health functional food for the prevention and improvement of diabetic complications.

The present invention also provides a use of The extract of *Homonoia riparia* Lour. or the fraction thereof for the production of a functional feed additive for the prevention and improvement of diabetic complications.

The present invention also provides a use of The extract of *Homonoia riparia* Lour. or the fraction thereof for the production of a composition for the inhibition of the advanced glycation endproducts production.

The present invention also provides a use of The extract of *Homonoia riparia* Lour. or the fraction thereof for the production of a pharmaceutical composition for the prevention and delay of aging.

The present invention also provides a use of The extract of *Homonoia riparia* Lour. or the fraction thereof for the production of a health functional food for the prevention and delay of aging.

The present invention also provides a use of The extract of *Homonoia riparia* Lour. or the fraction thereof for the production of a pharmaceutical composition for the prevention and treatment of cancer.

In addition, the present invention provides a use of The extract of *Homonoia riparia* Lour. or the fraction thereof for the production of a health functional food for the prevention and improvement of cancer.

Advantageous Effect

As explained hereinbefore, the extract of *Homonoia riparia* Lour. or the fractions thereof of the present invention inhibit the activity of aldose reductase and the generation of the advanced glycation endproducts, the index of diabetic complications, and have powerful activity of inhibiting diabetic complications with brining the anti-cataract, anti-retinopathy, and anti-neuropathy effect, and have the activity of anti-oxidation as well, so that they can be effectively used as an active ingredient of a pharmaceutical composition for the prevention and treatment of diabetic complications.

BRIEF DESCRIPTION OF THE DRAWINGS

The application of the preferred embodiments of the present invention is best understood with reference to the accompanying drawings, wherein:

FIG. 11 is a set of graphs illustrating the effect of the extract of *Homonoia riparia* Lour. on the loss of podocytes in type II diabetic animal model (SDT).

DESCRIPTION OF THE PREFERRED EMBODIMENTS

Figure 1:
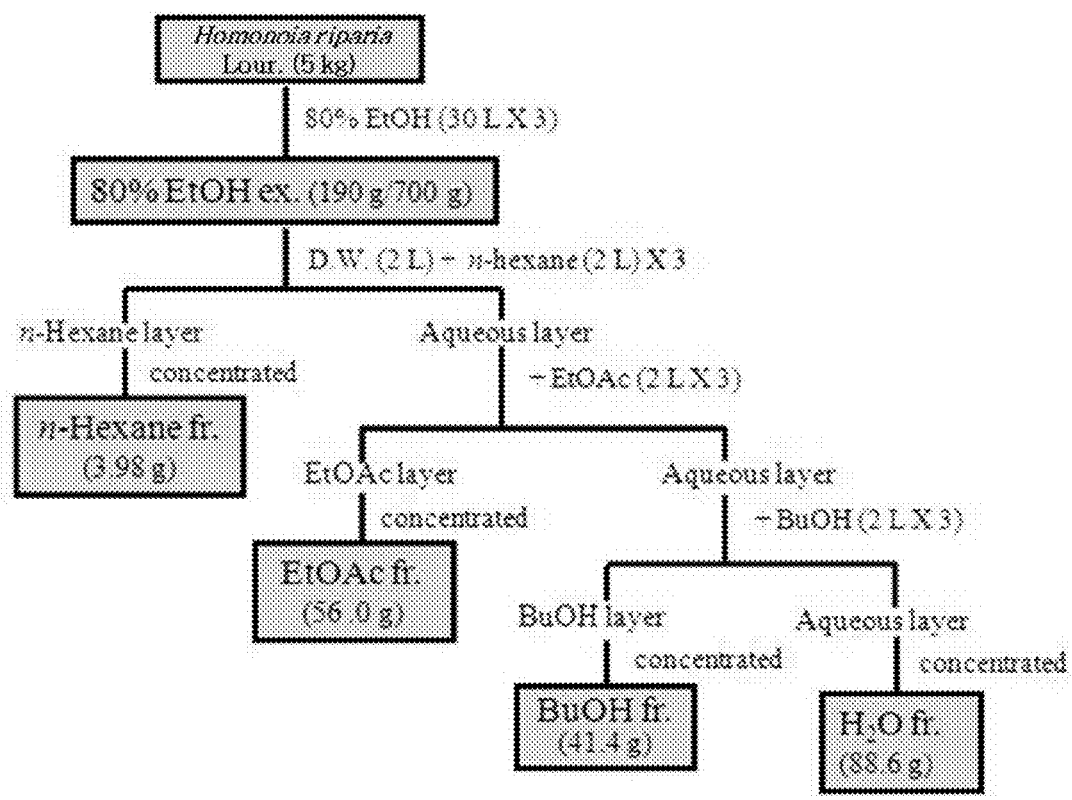
FIG. 1 is a diagram illustrating the extraction and line separation of *Homonoia riparia* Lour.

Hereinafter, the present invention is described in detail.

The present invention provides a pharmaceutical composition for the prevention and treatment of diabetic complications comprising the extract of *Homonoia riparia* Lour. or the fraction thereof as an active ingredient.

The present invention also provides a pharmaceutical composition for the prevention and treatment of diabetic complications comprising the fractions additionally obtained from the extract of *Homonoia riparia* Lour. by fractionation using an organic solvent as an active ingredient.

The present invention also provides a use of The extract of *Homonoia riparia* Lour. or the fraction thereof for the production of a pharmaceutical composition for the prevention and treatment of diabetic complications.

The said diabetic complication is preferably selected from the group consisting of diabetic retinopathy, diabetic cataract, diabetic nephropathy, diabetic neuropathy, heart disease, cancer, osteoporosis, and atherosclerosis, but not always limited thereto. Diabetic complications are the symptoms developed as diabetes continues for a long while. However, the standards for the judgment of occur and for the diagnosis are different from those of diabetes. The drugs to treat diabetic complications are also different and used independently from the drugs for diabetes.

The extract of *Homonoia riparia* Lour. is preferably prepared by the preparation method composed of the following steps, but not always limited thereto:

1) extracting *Homonoia riparia* Lour. using an extraction solvent;

2) cooling the extract obtained in step 1), followed by filtering thereof; and 3) concentrating the filtered extract of step 2) under reduced pressure, followed by drying thereof.

In the above method, the *Homonoia riparia* Lour. of step 1) is either obtained by cultivation or purchased. Any part of *Homonoia riparia* Lour. can be used but leaves or stems thereof are preferably used, but not always limited thereto.

The extraction solvent herein is water, alcohol, or the mixture thereof. The said alcohol is preferably $C_1$~$C_4$ lower alcohol. The lower alcohol herein is preferably ethanol or methanol and more preferably 80% methanol, but not always limited thereto. Alcohol having water content of 0.1%~50% can also be used. The extraction method herein is one of the conventional methods accepted in this field, which is exemplified by filtration, hot-water extraction, steeping, reflux extraction, and ultrasonification extraction. Herein, hot-water extraction is preferred. The extraction is preferably repeated 1~5 times and more preferably repeated 3 times, but not always limited thereto. The extraction solvent is added to the dried *Homonoia riparia* Lour. at the ratio of 1~10 times, more preferably 1~5 times the dried *Homonoia riparia* Lour. volume. The preferable temperature for the extraction is 20° C.~30° C., but not always limited thereto. The extraction hours are 24~48 hours, but not always limited thereto.

In the above method, the concentration under reduced pressure in step 3) is performed by using vacuum evaporator or rotary evaporator, but not always limited thereto. The drying process is performed by reduced-pressure drying, vacuum drying, boiling drying, spray drying, or freeze drying, but not always limited thereto.

In a preferred embodiment of the present invention, leaves and stems of *Homonoia riparia* Lour. were washed with water and dried in the shade. The dried leaves and stems were pulverized and loaded in an extraction vessel, to which an extraction solvent was added, followed by repeated extraction at room temperature. The obtained extract of *Homonoia riparia* Lour. was filtered to eliminate solid contents by using a filter paper. The extract was concentrated under reduced pressure to give the extract of *Homonoia riparia* Lour.

The fraction of *Homonoia riparia* Lour. extract is preferably prepared by the method containing the step of fractionating the extract of *Homonoia riparia* Lour. using an organic solvent, but not always limited thereto.

In the above method, the organic solvent is preferably normal-hexane, ethyl acetate, or normal-butanol, but not always limited thereto. The fraction herein is preferably obtained by repeating the fractionating process using the extract of *Homonoia riparia* Lour. 1~5 times, and more preferably 3 times, followed by concentration under reduced pressure, but not always limited thereto.

The fraction herein is preferably one of normal-hexane fraction, ethyl acetate fraction, normal-butanol fraction, or water fraction, obtained by fractionation using normal-hexane, ethyl acetate, normal-butanol, and water stepwise after suspending the extract of *Homonoia riparia* Lour. in water, but not always limited thereto.

In a preferred embodiment of the present invention, water and normal-hexane were added to the remnants obtained after evaporating the solvent from the extract of *Homonoia riparia* Lour. to separate normal-hexane layer. As a result, normal-hexane fraction was obtained. Water layer, except hexane layer, was mixed with ethyl acetate, followed by separating ethyl acetate layer to obtain ethyl acetate fraction. After eliminating the ethyl acetate layer, normal-butanol was added thereto and mixed to separate normal-butanol layer. As a result, normal-butanol fraction was obtained. Lastly, water fraction was obtained from water layer after eliminating the normal-butanol layer (see FIG. 1).

To evaluate the activity of inhibiting the production of advanced glycation endproducts which can be used as indices for of diabetic complications and treatment effect, binding degree of fructose and glucose was measured and used as an index using bovine serum albumin (BSA) as a protein. As for the positive control, aminoguanidine known to have excellent inhibiting effect on the production of the advanced glycation endproducts was used. As a result, the experimental group treated with the extract of *Homonoia riparia* Lour. or the fractions thereof demonstrated far more excellent activity of inhibiting the advanced glycation endproducts than the conventional aminoguanidine (see Table 1).

To examine the functions of the extract of *Homonoia riparia* Lour. or the fractions thereof, breaking effect on cross-linking between the advanced glycation endproducts and BSA was investigated. Particularly, ALT-711 (Alteon Inc., Ramsey, N.J.), known as AGEs cross-linker breaker, was compared with the extract of *Homonoia riparia* Lour. or the fractions thereof. As a result, it was confirmed that the extract of *Homonoia riparia* Lour. or the fractions thereof had excellent AGEs cross-linker breaking effect (see Table 2).

The present inventors measured the inhibiting effect of the extract of *Homonoia riparia* Lour. or the fractions thereof on aldose reductase activity, which is another index for diabetic complications. For the comparative control, 3,3-tetramethyleneglutaric acid was used. As a result, the extract of *Homonoia riparia* Lour. or the fractions thereof of the present invention were confirmed to suppress aldose reductase activity more efficiently than the conventional aldose reductase inhibitor (see Table 3).

The present inventors also investigated the preventive and therapeutic effect of the extract of *Homonoia riparia* Lour. on retinopathy and nephropathy in SDT (spontaneous diabetic torii) rat, the type II diabetic animal model. As a result, when the rat was treated with the extract of *Homonoia riparia* Lour., blood retinal barrier damage, pericyte loss, and acellular capillary generation, which were peculiar in diabetes group, were all significantly reduced (see FIG. 2 and FIG. 3), and the accumulation of the advanced glycation endproducts in retinal vessels and retinal neurons was also reduced (see FIG. 4). Besides, the decrease of apoptosis was also confirmed (see FIG. 5), suggesting that the extract of *Homonoia riparia* Lour. had diabetic retinopathy inhibiting effect. Further, significant decreases of renal indices and AGE and CML levels in urine or kidney were also confirmed by the treatment of the extract of *Homonoia riparia* Lour. (see FIG. 6, FIG. 7 and FIG. 8). The treatment of the extract also significantly reduced or inhibited glomerular basememebrane hyperplasia, mesangial matrix expansion, glomerular hypertrophy, glomerulosclerosis, collagen deposition, and podocyte loss (see FIG. 9, FIG. 10), suggesting that the extract could inhibit diabetic nephropathy efficiently.

Therefore, the extract of *Homonoia riparia* Lour. or the fractions thereof of the present invention were confirmed to have excellent activities of inhibiting the production of advanced glycation endproducts and aldose reductase activity, the indices for the evaluation of the effect of the therapeutic agent for diabetic complications, and treating diabetic complications in diabetic animal model. So, the extract of *Homonoia riparia* Lour. or the fractions thereof of the present invention can be effectively used as an active ingredient of a pharmaceutical composition for the prevention and treatment of diabetic complications.

The extract of *Homonoia riparia* Lour. or the fractions thereof can be included in the pharmaceutical composition of the present invention as an active ingredient at the concentration of 0.1~99.9 weight %. Any pharmaceutically acceptable carrier, excipient, or diluent can be added to the composition.

The composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the extract of *Homonoia riparia* Lour. with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The pharmaceutical composition of the present invention can be administered orally or parenterally. Particularly the composition of the present invention can be administered by external application, intraperitoneal injection, intrarectal injection, intravenous injection, intramuscular injection, subcutaneous injection, intrauterine injection or intracerebroventricular injection. More preferably, the composition is administered by external application.

The effective dosage of the composition of the present invention can be determined according to weight, age, gender, health condition, diet, administration frequency, administration method, excretion and severity of a disease. The dosage of the extract of *Homonoia riparia* Lour. is 0.01~1000 mg/kg per day, preferably 30~500 mg/kg per day, and more preferably 50~300 mg/kg per day. Administration frequency is once a day or preferably 1~6 times a day.

The composition of the present invention can be administered alone or treated together with surgical operation, radio-therapy, hormone therapy, chemo-therapy and biological regulators.

The present invention also provides a method for preventing diabetic complications containing the step of administering a pharmaceutically effective dose of the composition comprising the extract of *Homonoia riparia* Lour. or the fraction thereof as an active ingredient to a subject.

The present invention also provides a method for treating diabetic complications containing the step of administering a pharmaceutically effective dose of the composition comprising the extract of *Homonoia riparia* Lour. or the fraction thereof as an active ingredient to a subject having diabetic complications.

The subject herein is vertebrates and preferably mammals and more preferably such test animals as rats, rabbits, guinea pigs, hamsters, dogs and cats, and most preferably apes such as chimpanzees and gorillas.

The composition of the present invention can be administered orally or parenterally. Particularly the composition can be administered by intraperitoneal injection, intrarectal injection, subcutaneous injection, intravenous injection, intramuscular injection, intrauterine injection, intracerebroventricular injection, or intrathoracic injection.

Herein, the "pharmaceutically effective dose" indicates 0.0001~100 mg/kg, and more preferably 0.001~10 mg/kg, but not always limited thereto. The dose can be determined according to weight, age, gender, health condition, diet, administration frequency, administration method, excretion and severity of a disease.

The said diabetic complication is preferably selected from the group consisting of diabetic retinopathy, diabetic cataract, diabetic nephropathy, diabetic neuropathy, heart disease, cancer, osteoporosis, and atherosclerosis, but not always limited thereto.

The extract of *Homonoia riparia* Lour. or the fractions thereof of the present invention not only have the activities of inhibiting the production of advanced glycation endproducts, suppressing the aldose reductase activity, and breaking the cross-linking between the advanced glycation endproducts and protein, but also have the inhibiting effect on diabetic cataract, diabetic retinopathy, and diabetic nephropathy in type II diabetic animal model, suggesting that they have the diabetic complication inhibiting effect in vitro and in vivo. Therefore, the extract of *Homonoia riparia* Lour. or the fractions thereof of the present invention can be effectively used for the prevention and treatment of diabetic complications.

The present invention also provides a health functional food for the prevention and improvement of diabetic complications comprising the extract of *Homonoia riparia* Lour. or the fraction thereof as an active ingredient.

The present invention also provides a use of The extract of *Homonoia riparia* Lour. or the fraction thereof for the production of a health functional food for the prevention and improvement of diabetic complications.

The said diabetic complication is preferably selected from the group consisting of diabetic retinopathy, diabetic cataract, diabetic nephropathy, diabetic neuropathy, heart disease, cancer, osteoporosis, and atherosclerosis, but not always limited thereto.

The extract of *Homonoia riparia* Lour. or the fractions thereof of the present invention not only have the activities of inhibiting the production of advanced glycation endproducts, suppressing the aldose reductase activity, and breaking the cross-linking between the advanced glycation endproducts and protein, but also have the inhibiting effect on diabetic cataract, diabetic retinopathy, and diabetic nephropathy in type II diabetic animal model, suggesting that they have the diabetic complication inhibiting effect in vitro and in vivo. Therefore, the extract of *Homonoia riparia* Lour. or the fractions thereof of the present invention can be effectively used for the production of a health functional food for the prevention and improvement of diabetic complications.

The health functional food of the present invention can additionally include various flavors or natural carbohydrates, etc. The natural carbohydrates above can be one of monosaccharides such as glucose and fructose, disaccharides such as maltose and sucrose, polysaccharides such as dextrin and cyclodextrin, and glucose alcohols such as xilytol, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 weight part, and more preferably 0.02~0.03 weight part per 100 weight part of the health functional food of the present invention.

In addition to the ingredients mentioned above, the health functional food of the present invention can include a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The health functional food of the present invention can also include fruit flesh addable to natural fruit juice, fruit beverages and vegetable beverages. All the mentioned ingredients can be added singly or together. The mixing ratio of those ingredients does not matter in fact, but in general, each can be added by 0.01~0.1 weight part per 100 weight part of the health functional food of the present invention.

The present invention also provides a functional feed additive for the prevention and improvement of diabetic complications comprising the extract of *Homonoia riparia* Lour. or the fraction thereof as an active ingredient.

The present invention also provides a use of The extract of *Homonoia riparia* Lour. or the fraction thereof for the production of a functional feed additive for the prevention and improvement of diabetic complications.

The said diabetic complication is preferably selected from the group consisting of diabetic retinopathy, diabetic cataract, diabetic nephropathy, diabetic neuropathy, heart disease, cancer, osteoporosis, and atherosclerosis, but not always limited thereto.

The extract of *Homonoia riparia* Lour. or the fractions thereof of the present invention not only have the activities of inhibiting the production of advanced glycation endproducts, suppressing the aldose reductase activity, and breaking the cross-linking between the advanced glycation endproducts and protein, but also have the inhibiting effect on diabetic cataract, diabetic retinopathy, and diabetic nephropathy in type II diabetic animal model, suggesting that they have the diabetic complication inhibiting effect in vitro and in vivo. Therefore, the extract of *Homonoia riparia* Lour. or the fractions thereof of the present invention can be effectively used for the production of a feed additive for the prevention and improvement of diabetic complications.

By continuously administrating poultry and livestock with the said feed additive, diabetic complications can be prevented, and already developed diabetic complications can also be cured.

The feed additive of the present invention preferably includes the extract of *Homonoia riparia* Lour. or the fractions thereof 0.1~20 weight %, lipase 0.001~0.01 weight %, calcium phosphate (tribasic) 1~20 weight %, vitamin E 0.01~0.1 weight %, enzyme powder 1~10 weight %, lactic acid bacteria 0.1~10%, *bacillus* culture solution 0.01~10 weight %, and glucose 20~90 weight % by the total additive weight, but not always limited thereto. As long as the extract of *Homonoia riparia* Lour. or the fractions thereof of the present invention are included by the effective dosage, it can be used as the feed additive of the present invention.

The said effective dosage indicates the amount that can prevent diabetic complications by long term administration in poultry and livestock or that can treat diabetic complications already developed. It is though recommended not to use over-dose, more than the amount brining the positive effect, so as to prevent any negative effect.

The feed additive of the present invention can additionally include general carriers accepted in this field for poultry and livestock. In this invention, the feed additive can be used as it is or as mixed with other acceptable carriers and stabilizers, and if necessary, nutrients such as vitamins, amino acids, and minerals, or other additives such as antioxidants, antibiotics, antimicrobials, etc can be added. The feed additive can be formulated in the forms of powder, granule, pellet, and suspension. When supplied to poultry and livestock, the feed additive of the present invention can be given separately or mixed with feed.

The present invention also provides a composition for the inhibition of the advanced glycation endproducts production comprising the extract of *Homonoia riparia* Lour. or the fraction thereof as an active ingredient.

The present invention also provides a method for inhibiting the production of advanced glycation endproducts containing the step of administering a pharmaceutically effective dose of the composition comprising the extract of *Homonoia riparia* Lour. or the fraction thereof as an active ingredient to a subject.

The present invention also provides a use of The extract of *Homonoia riparia* Lour. or the fraction thereof for the production of a composition for the inhibition of the advanced glycation endproducts production.

The extract of *Homonoia riparia* Lour. or the fractions thereof of the present invention not only have the activities of inhibiting the production of advanced glycation endproducts, suppressing the aldose reductase activity, and breaking the cross-linking between the advanced glycation endproducts and protein, but also have the inhibiting effect on diabetic cataract, diabetic retinopathy, and diabetic nephropathy in type II diabetic animal model, suggesting that they have the diabetic complication inhibiting effect in vitro and in vivo. Therefore, the extract of *Homonoia riparia* Lour. or the fractions thereof of the present invention can be effectively used as an active ingredient of a composition for the inhibition of the advanced glycation endproducts production and for the production of the composition for the inhibition of the advanced glycation endproducts production. The extract of *Homonoia riparia* Lour. or the fractions thereof of the present invention can also be used for the method to inhibit the production of advanced glycation endproducts by administering a pharmaceutically effective dose of the same to a subject.

The present invention also provides a pharmaceutical composition for the prevention and delay of aging comprising the extract of *Homonoia riparia* Lour. or the fraction thereof as an active ingredient.

The present invention also provides a use of The extract of *Homonoia riparia* Lour. or the fraction thereof for the production of a pharmaceutical composition for the prevention and delay of aging.

The present invention also provides a health functional food for the prevention and delay of aging comprising the extract of *Homonoia riparia* Lour. or the fraction thereof as an active ingredient.

The present invention also provides a use of The extract of *Homonoia riparia* Lour. or the fraction thereof for the production of a health functional food for the prevention and delay of aging.

In the middle of the generation of the advanced glycation endproducts in hyperglycemic state, abnormal changes occur in lipid metabolism and at the same time toxic oxygen free-radical is generated. Then, defense system against such oxygen free-radical is reduced in the course, so that oxidative stress is induced (Yokozawa, T., et al, 2001, J. of Trad. Med., 18: 107-112). The extract of *Homonoia riparia* Lour. or the fractions thereof of the present invention inhibit effectively the generation of the advanced glycation endproducts, so that they can be efficiently used for a health functional food or a pharmaceutical composition for the prevention and delay of aging. The extract of *Homonoia riparia* Lour. or the fractions thereof of the present invention can be efficiently used for the production of a pharmaceutical composition or a health functional food for the prevention and delay of aging. The extract of *Homonoia riparia* Lour. or the fractions thereof of the present invention can be used for the method for inhibiting aging by administering a composition comprising a pharmaceutically effective dose of the same to a subject.

The present invention also provides a method for inhibiting aging containing the step of administering a pharmaceutically effective dose of a composition comprising the extract of *Homonoia riparia* Lour. or the fraction thereof as an active ingredient to a subject.

The extract of *Homonoia riparia* Lour. or the fractions thereof of the present invention inhibit the generation of the advanced glycation endproducts efficiently, so that they can be effectively used for the prevention and delay of aging.

The present invention also provides a pharmaceutical composition for the prevention and treatment of cancer comprising the extract of *Homonoia riparia* Lour. or the fraction thereof as an active ingredient.

The present invention also provides a use of The extract of *Homonoia riparia* Lour. or the fraction thereof for the production of a pharmaceutical composition for the prevention and treatment of cancer.

The present invention also provides a health functional food for the prevention and improvement of cancer comprising the extract of *Homonoia riparia* Lour. or the fraction thereof as an active ingredient.

The present invention also provides a use of The extract of *Homonoia riparia* Lour. or the fraction thereof for the production of a health functional food for the prevention and improvement of cancer.

It has been reported that the advanced glycation endproducts can induce cancer (Tokuda H. et al., 2005, Book of Abstract of 53rd GA Congress joint with SIF, P076). The extract of *Homonoia riparia* Lour. or the fractions thereof of the present invention inhibit efficiently the generation of the advanced glycation endproducts and have the effect of breaking the cross-linking between the advanced glycation endproducts and protein, so that they can be effective used for the production of a pharmaceutical composition for the prevention and treatment of cancer and for the production of a health functional food for the treatment and improvement of cancer.

The present invention also provides a method for the prevention of cancer containing the step of administering a pharmaceutically effective dose of the composition comprising the extract of *Homonoia riparia* Lour. or the fraction thereof as an active ingredient to a subject.

The present invention also provides a method for the treatment of cancer containing the step of administering a pharmaceutically effective dose of the composition comprising the extract of *Homonoia riparia* Lour. or the fraction thereof as an active ingredient to a subject having cancer.

The extract of *Homonoia riparia* Lour. or the fractions thereof of the present invention inhibit efficiently the generation of the advanced glycation endproducts and have the effect of breaking the cross-linking between the advanced glycation endproducts and protein, so that they can be effectively used for the method for the prevention of cancer by administering a composition comprising a pharmaceutically effective dose of the same to a subject or for the method for the treatment of cancer by administering a composition comprising a pharmaceutically effective dose of the same to a subject having cancer.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of *Homonoia riparia* Lour. Extract

<1-1> Ethanol Extract of *Homonoia riparia* Lour.

Leaves and twigs of *Homonoia riparia* Lour. (Voucher-specimen (no. TBRC-VN-118) is stored in Herbarium of Diabetic Complications Research Center, Division of Traditional Korean Medicine Integrated Research, Korea Institute of Oriental Medicine) were used. Leaves and twigs of *Homonoia riparia* Lour. purchased at Kyungdong Mart were chopped and pulverized, to which 80% ethanol was added. The prepared sample was loaded in the extraction vessel, followed by repeated extraction at room temperature. The extract was filtered and then concentrated under reduced pressure with maintaining the temperature as 40~45° C. in order to prevent decomposition and hydrolysis of the ingredients. As a result, 190 g of ethanol extract was obtained.

<1-2> Methanol Extract of *Homonoia riparia* Lour.

170 g of methanol extract of *Homonoia riparia* Lour. was prepared by the same manner as described in Example <1-1>, except that methanol was used instead of ethanol.

<1-3> Water Extract of *Homonoia riparia* Lour.

195 g of water extract of *Homonoia riparia* Lour. was prepared by the same manner as described in Example <1-1>, except that water was used instead of ethanol.

Example 2

Preparation of *Homonoia riparia* Lour. Fraction

<2-1> Normal-Hexane Fraction of *Homonoia riparia* Lour.

0.5 l of water and 0.5 l of normal-hexane were added to the ethanol extract of *Homonoia riparia* Lour. obtained in Example <1-1>. After mixing well, normal-hexane layer was separated. The said procedure was repeated three times. Then, the normal-hexane layer was concentrated under reduced pressure at 40° C. to give 3.98 g of normal-hexane fraction.

<2-2> Ethyl Acetate Fraction of *Homonoia riparia* Lour.

0.5 l of ethyl acetate was added to the water layer obtained in Example <2-1>. After mixing well, ethyl acetate layer was separated. The said procedure was repeated three times. Then, the ethyl acetate layer was concentrated under reduced pressure at 40° C. to give 56.0 g of ethyl acetate fraction.

<2-3> Normal-Butanol Fraction of *Homonoia riparia* Lour.

0.5 l of normal-butanol was added to the water layer obtained in Example <2-2>. After mixing well, normal-butanol layer was separated. The said procedure was repeated three times. Then, the normal-butanol layer was concentrated under reduced pressure at 40° C. to give 41.4 g of normal-butanol fraction.

<2-4> Water Fraction of *Homonoia riparia* Lour.

The water layer obtained in Example <2-3> was concentrated under reduced pressure at 40° C. to give 88.6 g of water fraction.

Experimental Example 1

Inhibiting Effect on the Advanced Glycation Endproducts Production

Inhibiting effect of the extract of *Homonoia riparia* Lour. obtained in <Example 1> and each fraction thereof (normal-hexane, ethyl acetate, normal-butanol, or water fraction) obtained in <Example 2> on the advanced glycation endproducts production was investigated in vitro. Bovine serum albumin (BSA, Sigma, USA) was used as a protein source. BSA was added to 50 mM phosphate buffer (pH 7.4) to make the concentration 10 mg/ml. 0.2 M fructose/0.2 M glucose mixed solution was used as a sugar source. The fructose/glucose mixed solution was added to the BSA solution prepared above. The ethanol extract of *Homonoia riparia* Lour. was prepared at the concentration of 2.5 µg/ml, 5 µg/ml, or 10 µg/ml. The normal-hexane fraction was prepared at the concentration of 10 µg/ml, 25 µg/ml, or 50 µg/ml. The ethyl acetate fraction was prepared at the concentration of 1.25 µg/ml, 2.5 µg/ml, or 5 µg/ml. The normal-butanol fraction was prepared at the concentration of 1.25 µg/ml, 2.5 µg/ml, or 5 µg/ml. The water fraction was prepared at the concentration of 2.5 µg/ml, 5 µg/ml, or 10 µg/ml. All the compounds were dissolved in dimethylsulfoxide (DMSO), to which 15% tween 80 was added. At that time, the final DMSO content was 0.2%. The prepared extract or the fractions thereof were added to the BSA/sugar mixed solution, followed by culture for 14 days at 37° C. At that time, 0.02% sodium azide and antimycotics were added as an anti-bacterial agent and an anti-fungal agent. The BSA/sugar mixed solution was cultured, which was used as the control. The extract or the fractions thereof were used as the blank. In the meantime, aminoguanidine was used as the positive control, which was the index for the effect comparison. Particularly, aminoguanidine was dissolved in distilled water, followed by culture by the same manner as described above at the concentration of 18.5 µg/ml, 37 µg/ml, or 55.5 µg/ml for 14 days. All the culture solutions were prepared 4 of each to minimize error. After 14 days of culture, the amount of the advanced glycation endproducts was measured. The advanced glycation endproducts were fluorescent brown and had physiochemical property suitable for cross-linking, and also had ligands which could be recognized by cell membrane receptors. The amount of the advanced glycation endproducts having the said properties was measured by a microplate reader (Excitation: 350 nm, Emission: 450 nm) to evaluate the inhibiting effect on the advanced glycation endproducts production (Vinson, J. A. et al., *J. Nutr. Biochem.*, 7: 659-663, 1996). Inhibition rate of the advanced glycation endproducts production was calculated by the following mathematical formula 1.

Inhibition Rate (%)=100−(Fluorescent Intensity of Experimental Group−Fluorescent Intensity of Experimental Blank Group)/(Fluorescent Intensity of Control Group−Fluorescent Intensity of Control Blank Group)×100     [Mathematical Formula 1]

As a result, as shown in Table 1, the half maximal inhibitory concentrations ($IC_{50}$) for the advanced glycation endproducts production of the ethanol extract, methanol extract, and water extract of *Homonoia riparia* Lour., and normal-hexane fraction, ethyl acetate fraction, normal-butanol fraction, and water fraction of the ethanol extract were 5.67 µg/ml, 6.59 µg/ml, 6.75 µg/ml, 50 µg/ml, 4.68 µg/ml, 4.53 µg/ml, and 8.49 µg/ml, respectively. These values were much higher than that of aminoguanidine (the positive control, $IC_{50}$: 52.96 µg/ml), respectively 9.3 fold, 8.0 fold, 7.8 fold, 11.3 fold, 11.7 fold, and 6.2 fold higher, indicating more excellent effect. Among the extracts, ethanol extract had the highest inhibiting effect (Table 1). The extract of *Homonoia riparia* Lour. or the fractions thereof of the present invention had been confirmed to inhibit the cross-linking of protein and sugar and hence inhibit the advanced glycation endproducts production. The ethanol extract confirmed to have the most excellent inhibiting effect on the advanced glycation endproducts production was used for the investigation of the effect on diabetic complications.

TABLE 1

| | Conc. (µg/ml) 14th day | Inhibition (%) 14th day | $IC_{50}$ (µg/ml) 14th day |
|---|---|---|---|
| Ethanol extract of *Homonoia riparia* Lour. | 2.5 | 26.26 ± 2.64 | 5.67 ± 0.24 |
| | 5 | 47.55 ± 1.03 | |
| | 10 | 79.52 ± 1.46 | |
| Methanol extract of *Homonoia riparia* Lour. | 2.5 | 23.20 ± 1.04 | 6.59 ± 0.21 |
| | 5 | 44.35 ± 1.08 | |
| | 10 | 76.71 ± 1.33 | |
| Water extract of *Homonoia riparia* Lour. | 2.5 | 22.16 ± 1.61 | 6.75 ± 1.12 |
| | 5 | 43.11 ± 1.56 | |
| | 10 | 75.13 ± 1.07 | |
| Normal-hexane fraction of *Homonoia riparia* Lour. ethanol extract | 10 | 13.06 ± 2.46 | >50 |
| | 25 | 17.62 ± 2.05 | |
| | 50 | 23.77 ± 3.09 | |
| Ethyl acetate fraction of *Homonoia riparia* Lour. ethanol extract | 1.25 | 19.58 ± 3.60 | 4.68 ± 0.28 |
| | 2.5 | 33.59 ± 1.62 | |
| | 5 | 52.06 ± 2.85 | |
| Normal-butanol fraction of *Homonoia riparia* Lour. ethanol extract | 1.25 | 21.86 ± 1.29 | 4.53 ± 0.25 |
| | 2.5 | 34.61 ± 3.12 | |
| | 5 | 53.45 ± 1.73 | |
| Water fraction of *Homonoia riparia* Lour. ethanol extract | 2.5 | 24.02 ± 3.03 | 8.49 ± 0.38 |
| | 5 | 35.40 ± 2.51 | |
| | 10 | 56.32 ± 1.40 | |
| Aminoguanidine | 18.5 | 15.50 ± 1.79 | 52.96 ± 1.95 |
| | 37 | 33.56 ± 0.51 | |
| | 55.5 | 52.81 ± 2.81 | |

Experimental Example 2

In Vitro Analysis of AGE Cross-Linking Breaking Effect 1.0 µg of AGE-BSA was distributed in a collagen-coated 96-well microtitre plate, followed by culture for 4 hours at 37° C. The plate was then washed with PBS containing 0.05% tween three times to eliminate non-conjugated AGE-BSA. *Homonoia riparia* Lour. The extract of *Homonoia riparia* Lour. or ALT-711 (4,5-dimethyl-3-(2-oxo-2-phenylethyl)-thiazolium chloride; Alteon Inc., Ramsey, N.J.) known as the AGEs cross-linking breaker was 2-fold diluted serially from the concentration of 1000 µg/ml to 1 µg/ml, which was added to each well (triplicate), followed by culture for 4 hours at 37° C. Upon completion of the culture, each well was washed with PBS containing 0.05% tween three times. To detect the AGE-BSA remaining as cross-linked to collagen, rabbit polyclonal anti-AGE-BSA antibody (MBL international, Woburn, Mass.) diluted at the ratio of 1:250 was distributed in each well, followed by culture for 1 hour at 37° C. One hour later, the plate was washed with PBS containing 0.05% tween three times, to which horseradish peroxidase-linked goat anti-rabbit antibody (Sigma, USA) was applied. Color development was induced by using 3,3',5,5'-tetramethylbenzidine (TMB) as a substrate and $OD_{450}$ was measured. Breaking % of AGE-BSA cross-linking was calculated by the following mathematical formula 2.

AGE-BSA (%)=OD of sample treated well/OD of sample untreated well×100     [Mathematical Formula 2]

As a result, as shown in Table 2, AGE-BSA cross-linking breaking effect of the extract of *Homonoia riparia* Lour. was at least 38 fold more excellent than that of the control ALT-711 (Table 2).

TABLE 2

| | Conc. (μg/ml) | | | | | $IC_{50}$ |
|---|---|---|---|---|---|---|
| | 0 | 10 | 50 | 100 | 1000 | (μg/ml) |
| Ethanol extract of *Homonoia riparia* Lour. | 100.00 ± 7.43 | 73.00 ± 4.79 | 24.70 ± 1.09 | 18.45 ± 0.94 | 17.10 ± 1.92 | 26.13 ± 2.74 |
| ALT-711 | 100.00 ± 26.69 | 100.18 ± 18.4 | 100.13 ± 4.42 | 100.21 ± 5.46 | 51.77 ± 9.54 | >1000 |

Experimental Example 3

Inhibiting Effect on Aldose Reductase (AR) Activity

Inhibiting effect of the extract of *Homonoia riparia* Lour. or the fractions (normal-hexane fraction, ethyl acetate fraction, normal-butanol fraction, and water fraction) thereof on aldose reductase activity was investigated in vitro. To obtain natural aldose reductase from the eyeball of SD rat (Sprague-Dawley rat, 250~280 g) according to the method of Dufrane (1984), 135 mM Na, K-phosphate buffer (pH 7.0), and 10 mM 2-mercaptoethanol were mixed with the extracted lens, which was ground by using a homogenizer and a sonicater. After performing centrifugation at 14,000 rpm for 30 minutes, the supernatant was filtered by using 0.2 μm filter. All the procedures were performed at 4° C. Quantification was performed by Lowry method using BSA as a protein source of the enzyme. The mixture comprising 135 mM Na, K-phosphate buffer (pH 7.0), 100 mM lithium sulfate, 0.03 mM NADPH, 0.04 mM DL-glycealdehyde and 100 μg/ml enzyme mixture was dissolved in 0.1% DMSO, which was distributed to 50 μl of each sample diluted at different concentrations by 50 μl to make the total volume 1 ml, followed by culture for 10 minutes at 37° C. The experimental blank group was added with the mixture excluding 0.04 mM DL-glycealdehyde, and STD was treated with the sample including 135 mM Na, K-phosphate buffer (pH 7.0), 100 mM lithium sulfate, and 50 μl of NADP (0.2~5 μM). The reaction was terminated by adding 0.3 ml of 0.5 N HCl. 1 ml of 6 M NaOH including 10 mM imidazole was added thereto, followed by reaction at 60° C. for 10 minutes. Then, the conversion of NADP to fluorescent product was measured. The examination was performed in triplicate. The effect was measured by using a spectrofluorophotometric detector (Bio-TEK, Synergy HT, USA) (Ex. 360 nm, Em. 460 nm) and presented as $IC_{50}$. The extract of *Homonoia riparia* Lour. was prepared at the concentration of 1 μg/ml, 2.5 μg/ml, or 5 μg/ml. The normal-hexane fraction was prepared at the concentration of 2.5 μg/ml, 5 μg/ml, or 10 μg/ml. The ethyl acetate fraction was prepared at the concentration of 0.5 μg/ml, 1 μg/ml, or 2.5 μg/ml. The normal-butanol fraction was prepared at the concentration of 1 μg/ml, 2.5 μg/ml, or 5.0 μg/ml. The water fraction was prepared at the concentration of 2.5 μg/ml, 5 μg/ml, or 10 μg/ml. As the comparative control group, one of the excellent aldose reductase inhibitors, 3,3-tetramethyleneglutaric acid, was prepared at the concentration of 3.72 μg/ml, 4.66 μg/ml, or 5.59 μg/ml. Then, AR inhibiting effect of each sample was measured.

As a result, as shown in Table 3, the AR inhibiting effect of the extract of *Homonoia riparia* Lour., and the normal-hexane fraction, the ethyl acetate fraction, the normal-butanol fraction and the water fraction thereof was respectively presented as $IC_{50}$ values of 2.60 μg/ml, 5.58 μg/ml, 1.20 μg/ml, 3.35 μg/ml, and 7.19 μg/ml. The effect of the extract of *Homonoia riparia* Lour., and the ethyl acetate fraction and the normal-butanol fraction thereof was respectively 2.3-fold, 4.5-fold, and 1.6-fold higher than that of the positive control 3,3-tetramethyleneglutaric acid ($IC_{50}$: 5.41 μg/ml) (Table 3). Therefore, it was confirmed that the AR inhibiting effect of the extract of *Homonoia riparia* Lour., or the ethyl acetate fraction and the normal-butanol fraction thereof was significantly excellent, compared with the single synthetic compound.

TABLE 3

| | Effect | | |
|---|---|---|---|
| Extract | Conc. (μg/ml) | Inhibiting effect (%) | Inhibiting effect ($IC_{50}$) (μg/ml) |
| Ethanol extract of *Homonoia riparia* Lour. | 1 | 33.60 ± 2.50 | 2.60 ± 0.37 |
| | 2.5 | 48.40 ± 6.35 | |
| | 5 | 75.60 ± 3.67 | |
| Normal-hexane fraction of *Homonoia riparia* Lour. extract | 2.5 | 37.50 ± 2.54 | 5.58 ± 0.60 |
| | 5 | 49.04 ± 6.93 | |
| | 10 | 65.71 ± 1.47 | |
| Ethyl acetate fraction of *Homonoia riparia* Lour. extract | 0.5 | 33.62 ± 6.76 | 1.20 ± 0.09 |
| | 1 | 48.94 ± 2.21 | |
| | 2.5 | 75.32 ± 6.06 | |
| Normal-butanol fraction of *Homonoia riparia* Lour. extract | 1 | 19.58 ± 5.96 | 3.35 ± 0.06 |
| | 2.5 | 40.91 ± 3.97 | |
| | 5 | 69.93 ± 0.61 | |
| Water fraction of *Homonoia riparia* Lour. extract | 2.5 | 22.03 ± 6.82 | 7.19 ± 0.83 |
| | 5 | 42.31 ± 5.84 | |
| | 10 | 63.64 ± 3.97 | |
| 3,3-tetramethyleneglutaric acid | 3.72 | 33.03 ± 4.36 | 5.41 ± 0.13 |
| | 4.66 | 40.27 ± 1.36 | |
| | 5.59 | 51.58 ± 0.78 | |

Experimental Example 4

Effect on Type II Diabetic Animal Model

<4-1> Raising Type II Diabetic Animal Model and Administration of the Extract of *Homonoia riparia* Lour.

To investigate the effect of the extract of *Homonoia riparia* Lour. on the prevention and treatment of diabetic complications in spontaneous diabetic Torii (SDT) rats, the type II diabetic animal model, the extract of *Homonoia riparia* Lour. was orally administered to the animal for 16 weeks. 10-week old male SDT rats (CLEA Japan Inc., Tokyo, Japan) were adapted for 1 week, and then continued to raise for 15 weeks until the blood sugar level reached 300 mg/dl. Feed and water were provided freely. 15 weeks later, the rats were grouped into 5 group (8 rats per group), to which the extract of *Homonoia riparia* Lour. (HR) and the control drug MET were administered orally once a day. The experimental groups included the normal group (NOR), the diabetic group (DM), the metformin (350 mg/kg) treated diabetic group (MET), the *Homonoia riparia* Lour. extract (100 mg/kg) treated diabetic group (HR-100), and the *Homonoia riparia* Lour. extract (250 mg/kg) treated diabetic group (HR-250). Each group was administered with the test samples orally once a day for 16 weeks. Urine was picked up 24 hours before autopsy. The organs extracted by autopsy were stored at −80° C.

<4-2> Inhibition of Diabetic Retinopathy in Type II Diabetic Animal Model

<4-2-1> Blood-Retinal Barrier Breakage

When hyperglycemic state continues, retinal vessels in eyeball become mal-functioning to cause blood-retinal barrier breakage. Therefore, the effect of the extract of *Homonoia riparia* Lour. of the present invention on the prevention of blood-retinal barrier breakage. For the autopsy of the rat of Example <4-1>, pentobarbital sodium (25 mg/kg weight) was administered by intraperitoneal injection to anesthetize the animal. Abdominal cavity and the abdomen and thoracic cavity of the anesthetized rat were opened to reach the heart. 50 mg/ml of fluorescein-dextran (molecular weight: $2\times10^6$) dissolved in 1 ml/ml of sterilized PBS was injected in the left ventricle. 10 minutes later, eyeball was extracted. Retina of the left eyeball was separated from eyecup. The separated retina was placed on the slide, followed by mounting with aqueous mounting medium. After drying thereof completely, the retina was observed under fluorescent microscope.

Figure 2:
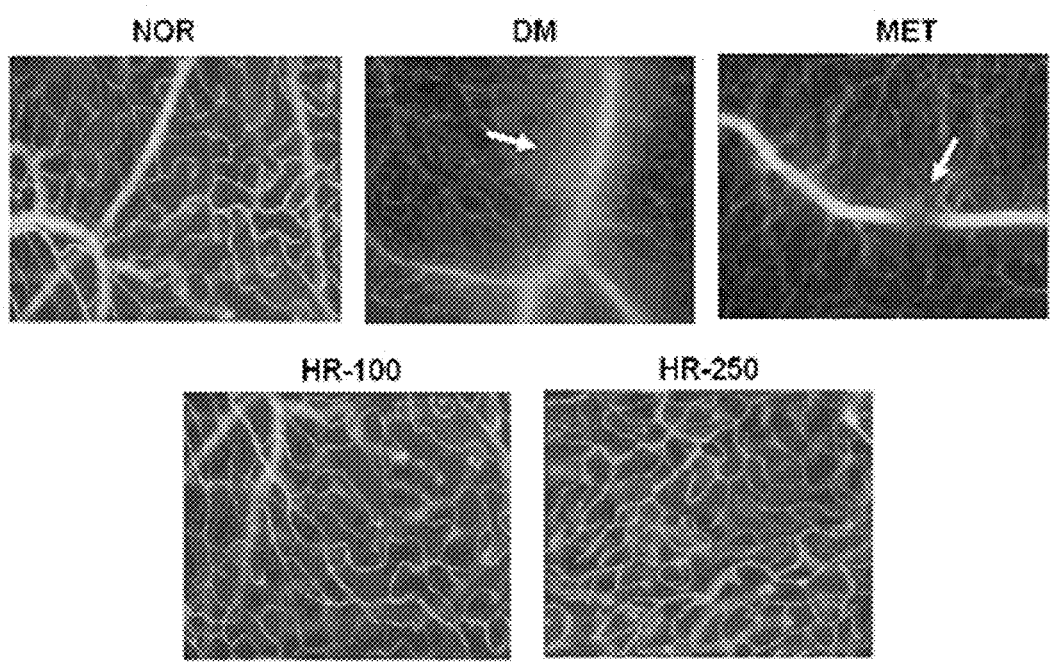
FIG. 2 is a set of photographs illustrating the effect of the extract of *Homonoia riparia* Lour. on angiogenesis in type II diabetic animal model (SDT).

As a result, as shown in FIG. 2, fluorescence was not observed in the normal group (NOR), while fluorescent material was flown out of blood vessels because of the blood-retinal barrier breakage in multiple subjects in the diabetic group (DM), presented by the arrow. Some cases of non-perfusion area (arrow), generated when blood vessels were narrowed, were also observed. In the metformin treated group (MET), fluorescence material was merely observed. In the *Homonoia riparia* Lour. extract treated diabetic group (HR-100 or HR-250), the above phenomenon was not observed.

<4-2-2> Inhibiting Effect on Pericyte Loss and Acellular Capillary Formation

The representative early symptoms of diabetic retinopathy are loss of pericyte, one of retinal vessel components, and acellular capillary formation. Thus, retinal vessels were first separated to investigate pericyte loss and acellular capillary formation. Particularly, retina was extracted from the right eyeball of the rat, which was washed with tap water, followed by culture in 3% trypsin for 1 hour at 37° C. The decomposed retina was placed in PBS and internal membrane was eliminated. Vascular frame was separated from retinal background by using a glass rod, which was placed on the slide and dried. Changes in cell wall and nucleus were observed by PAS and hematoxylin staining.

Figure 3:
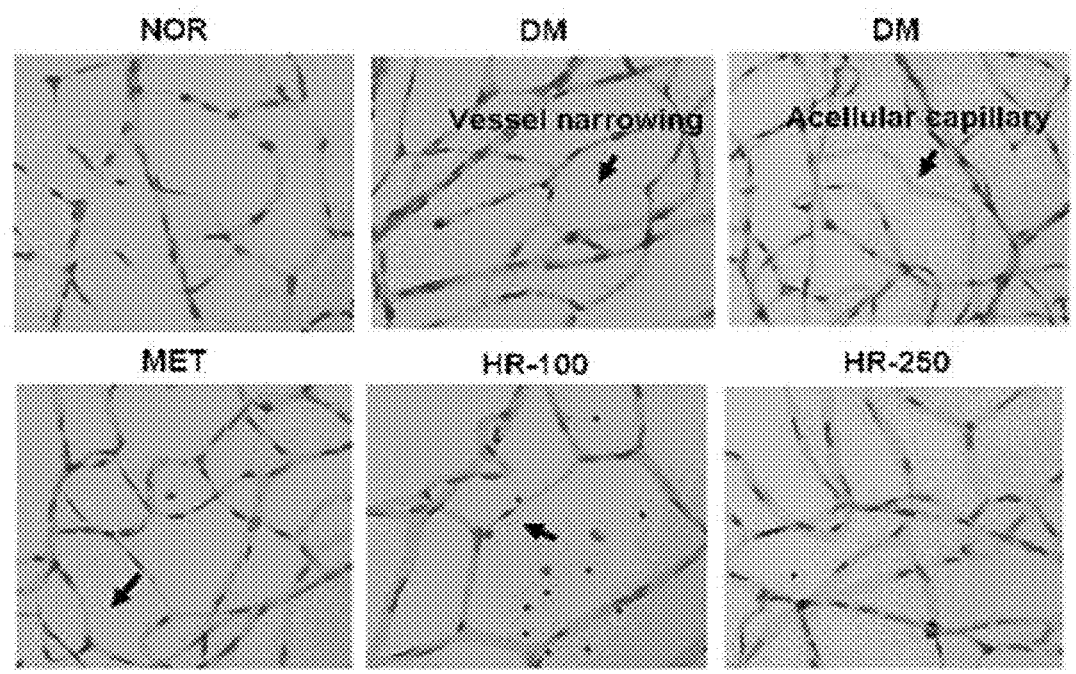
FIG. 3 is a set of photographs illustrating the effect of the extract of *Homonoia riparia* Lour. on the loss of pericytes and the generation of acellular capillaries in type II diabetic animal model (SDT).

As a result, as shown in FIG. 3, pericyte loss, acellular capillary formation accompanying vascular endothelial cell loss, and closed vessels were observed. Pericyte loss, acellular capillary formation, and closed vessels were significantly increased in the diabetic group, but significantly decreased in the metformin treated group (MET) or the *Homonoia riparia* Lour. extract treated group (HR-100 or HR-250) (FIG. 3).

<4-2-3> Preventive Effect on the Accumulation of Advanced Glycation Endproducts (AGEs) in Retinal Vessels and Retinal Neurons Upon completion of deparaffinization and hydration, the slide was reacted in 3% hydroxy peroxide solution for 10 minutes to deactivate endogenous peroxidase activity. The slide was then washed with PBS containing 0.05% tween 20 three times. To eliminate non-specific reaction, blocking was performed with 5% casein. The primary antibody anti-AGEs (Cosmo Bio) and anti-GFAP antibody (Santacurz) were diluted at the ratio of 1:200, which were treated to the slide for 1 hour. After washing the slide with PBS for one hour, the slide was treated with labeled streptoavidin biotin (LSAB) kit (Dako, USA) or FITC-conjugated secondary antibody, followed by color development by using DAB. Changes of AGEs were observed under fluorescent microscope and optical microscope.

Figure 4:
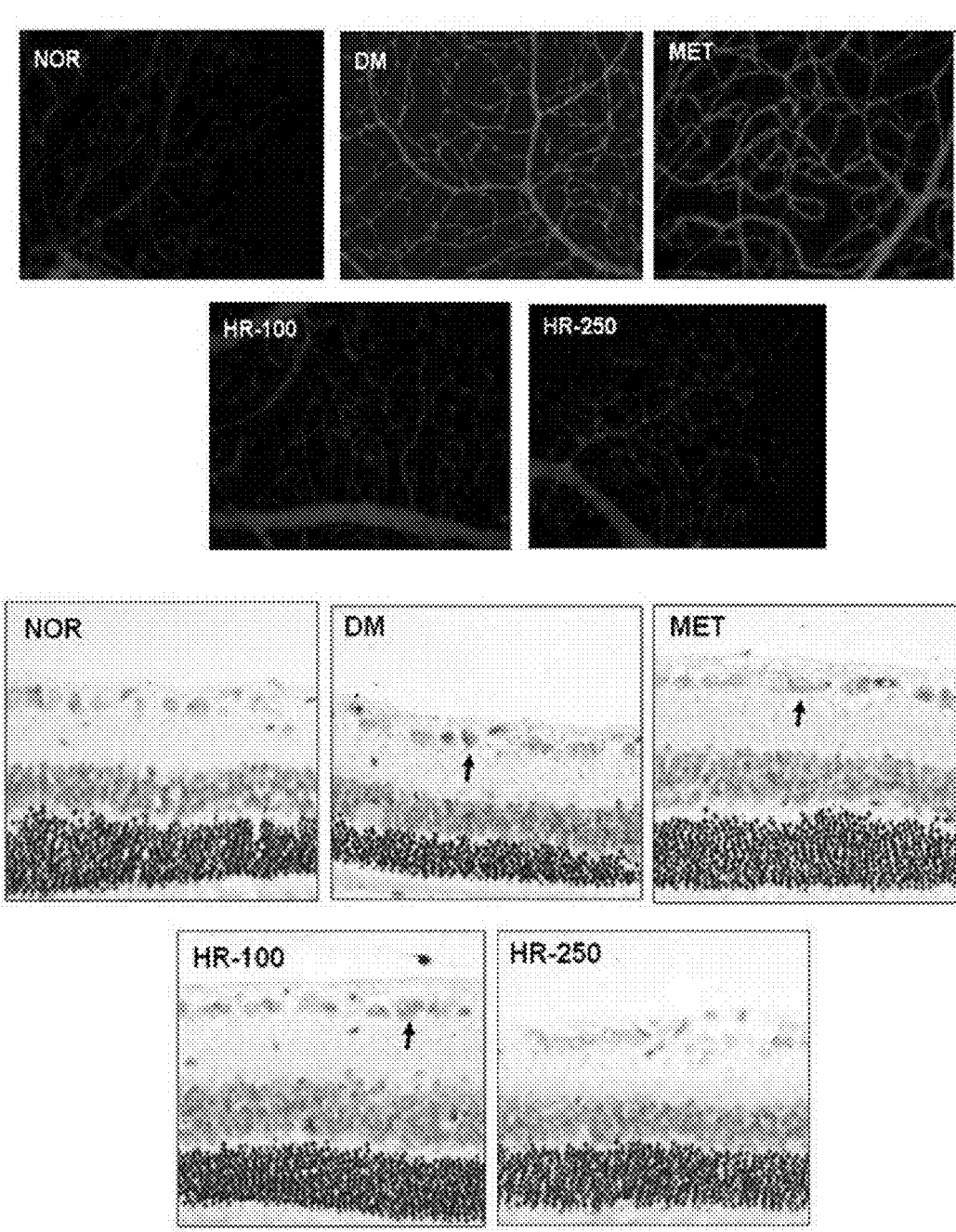
FIG. 4 is a set of photographs illustrating the effect of the extract of *Homonoia riparia* Lour. on the accumulation of the advanced glycation endproducts in retinal vessels (left) and retinal neurons (right) in type II diabetic animal model (SDT).

As a result, as shown in FIG. 4, the accumulation of the advanced glycation endproducts, which are the causing material of diabetic complications, in retinal vessels and retinal neurons was increased in the diabetic group (DM), compared with in the normal group (NOR). However, the accumulation of the advanced glycation endproducts was significantly reduced in the *Homonoia riparia* Lour. extract treated group, particularly in the group treated with high concentration of the extract (HR-250), which was even greater than in the metformin treated group (MET) (FIG. 4).

<4-2-4> Preventive Effect on Apoptosis of Retinal Vessel Cells and Retinal Neurons Tissue sections were deparaffinized and hydrated. After washing with PBS, the tissue sections were treated in proteinase K (20 μg/ml) solution for 15 minutes at 37° C. The tissue sections were washed with PBS again, followed by reaction in TUNEL reaction mixture solution (In situ cell death detection kit, AP, Roche, Germany) for 1 hour at 37° C. Retinal vessel pericyte loss and retinal neuron loss were observed under fluorescent microscope. TUNEL staining was performed to confirm the observed loss was attributed to apoptosis.

Figure 5:
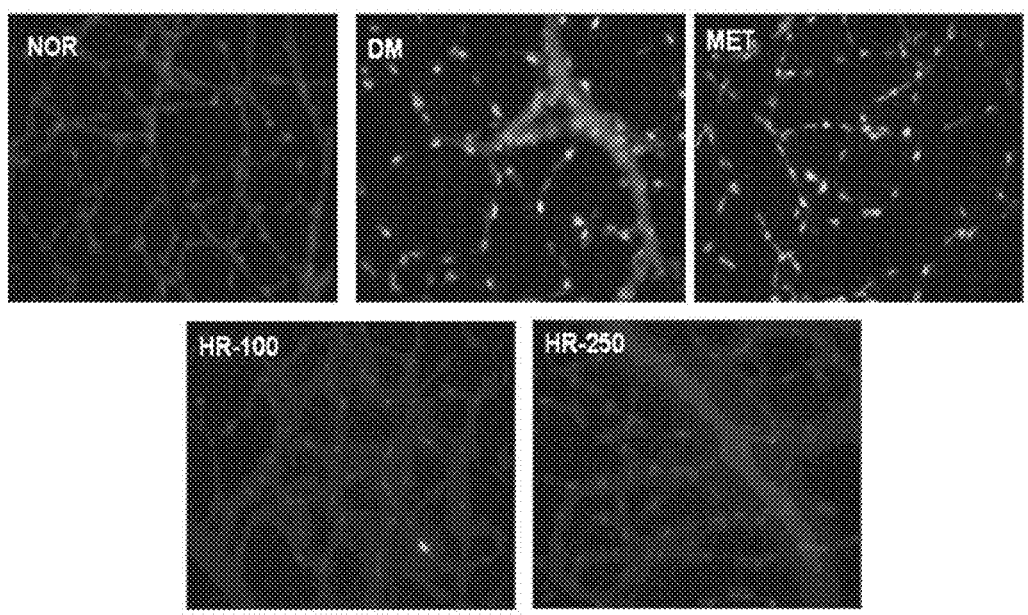
FIG. 5 is a set of photographs illustrating the effect of the extract of *Homonoia riparia* Lour. on the prevention of apoptosis in retinal vessels (left) and retinal neurons (right) in type II diabetic animal model (SDT).
Figure 5:
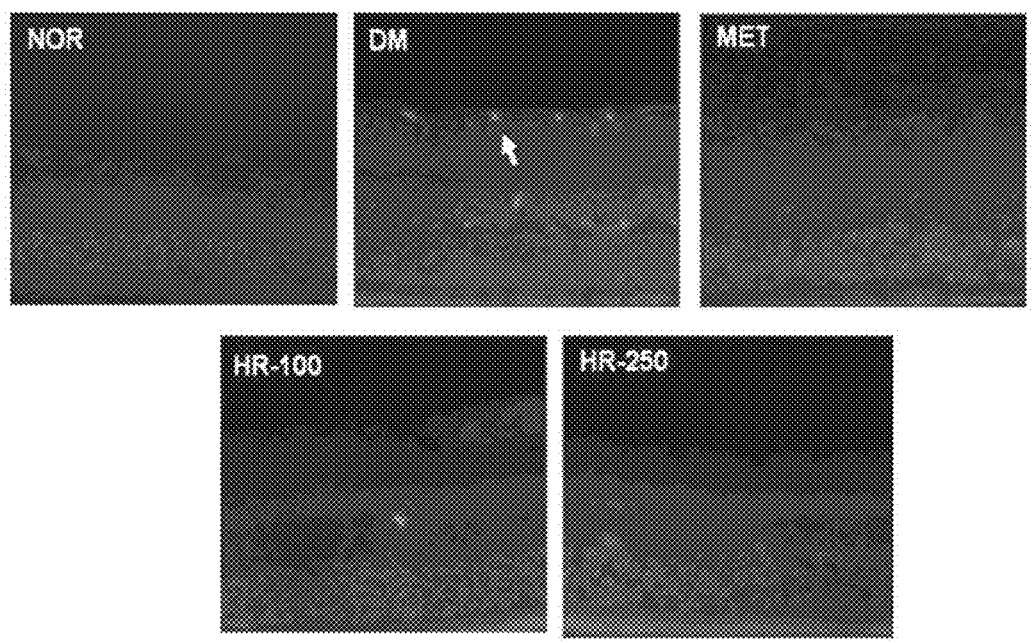

As a result, as shown in FIG. 5, TUNEL positive cells were significantly increased in the diabetic group, compared with in the normal group. *Homonoia riparia* Lour. Apoptosis of retinal vessel cells and retinal neurons was significantly reduced in the group treated with the extract of *Homonoia riparia* Lour. (HR-100 or HR-250) (FIG. 5).

<4-3> Investigation on Diabetic Nephropathy in Type II Diabetic Animal Model

<4-3-1> Analysis of Renal Indices, AGEs and CML

To investigate the effect of the extract of *Homonoia riparia* Lour. on the functions of the kidney suffering from chronic diabetes, urine was taken from the animal model 24 hours before the autopsy, with which renal indices {proteinuria, albuminuria, and glomerular filtration rate (Ccr)}, and glycation products (AGES and CML) were quantified. ELISA was performed to measure proteinuria, albuminuria, glomerular filtration rate, AGEs, CML, and podocyte (synaptopodin and WT-1). Particularly, the urine sample was mixed with coating buffer (50 mM carbonate buffer, pH 9.6) to make the final volume to be 100 μl (1:2), which was distributed in a 96-well plate. The plate stood at 37° C. for 3 hours and then washed with 0.05% PBST three times, followed by blocking with 3% skim milk. The plate stood as it was for 1 more hour and then washed. AGEs (Transgenic, JAPAN), CML (Transgenic, JAPAN), albumin, synaptopodin, and WT-1 (Santa Cruz, USA) antibodies were diluted respectively at the ratio of 1:1000, which were loaded in each well of the plate by 100 μl. The plate stood at 37° C.

for 2 hours, and washed with 0.05% PBST. HRP-conjugated secondary antibody was loaded in each well of the plate by 100 μl, followed by reacting at 37° C. for 1 hour. 100 μl of the substrate, 3,3',5,5'-tetramethylbenzidine (TMB) in 0.05% PBST was added to each well of the plate. 5 minutes later, the reaction was terminated by adding 1M $H_2SO_4$ solution (100 μl/well). Then OD was measured with an ELISA reader.

Immunological staining was performed as follows. After deparaffinization and hydration, the slide was reacted in 3% $H_2O_2$ solution for 10 minutes to deactivate endogenous peroxidase activity therein. Then, the slide was washed with PBS containing 0.05% tween 20 three times. To eliminate non-specific reaction, the slide was blocked with 5% AFB (animal free bock). The primary antibodies AGEs (Transgenic, Japan) and CML (Transgenic, Japan) were diluted (1:1000) and treated to the slide for 1 hour or overnight. After washing with PBS for 1 hour, the slide was treated with labeled streptavidin biotin (LSAB) kit (Dako, USA), followed by color development by using DAB (Dako, USA). Observation was performed under optical microscope.

Figure 6:
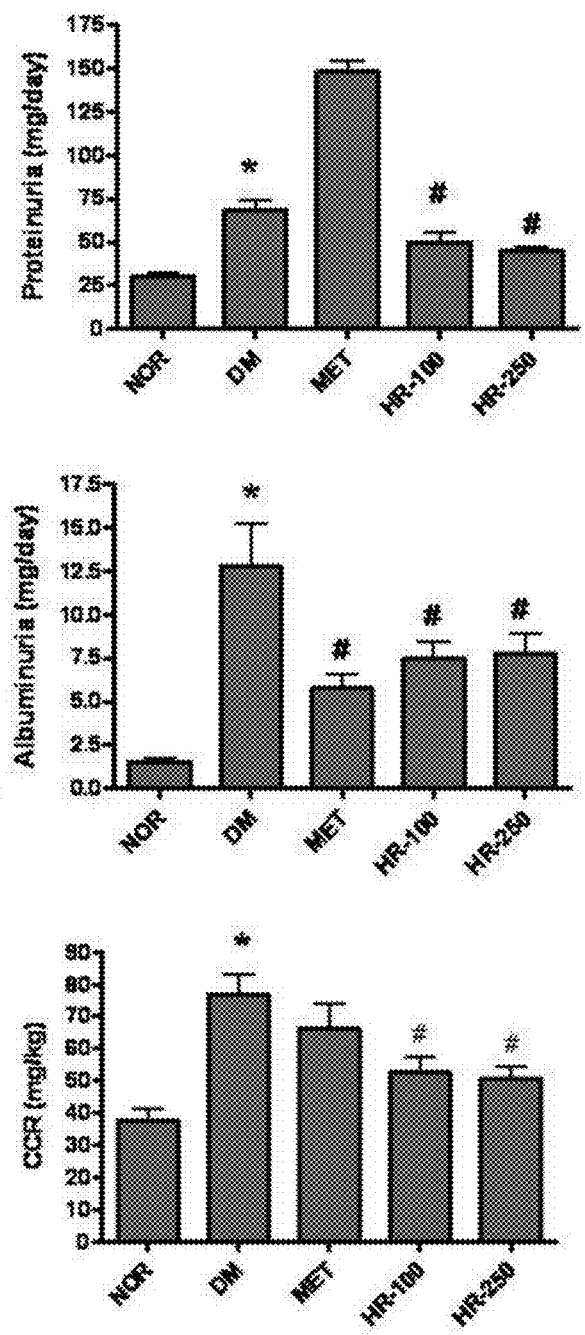
FIG. 6 is a set of graphs illustrating the effect of the extract of *Homonoia riparia* Lour. on the prevention of apoptosis on proteinuria, albuminuria, and glomerular filtration rate, which are the renal indices, in retinal vessels (left) and retinal neurons (right) in type II diabetic animal model (SDT).
Figure 7:
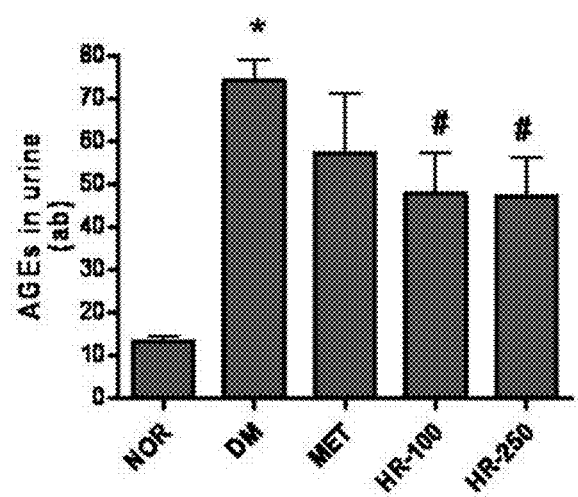
FIG. 7 is a set of graphs illustrating the effect of the extract of *Homonoia riparia* Lour. on the levels of the advanced glycation endproducts and CML in urine of type II diabetic animal model (SDT).
Figure 7:
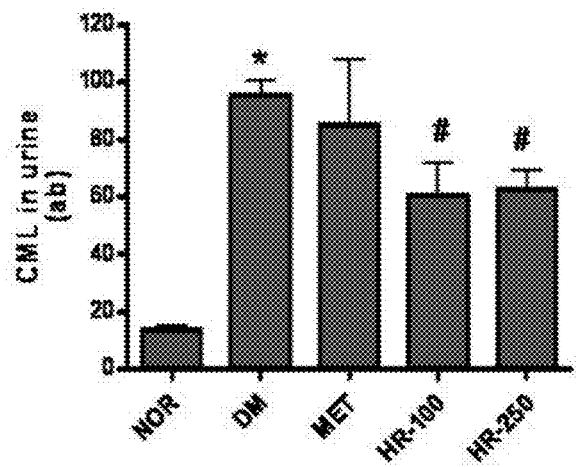
Figure 8:
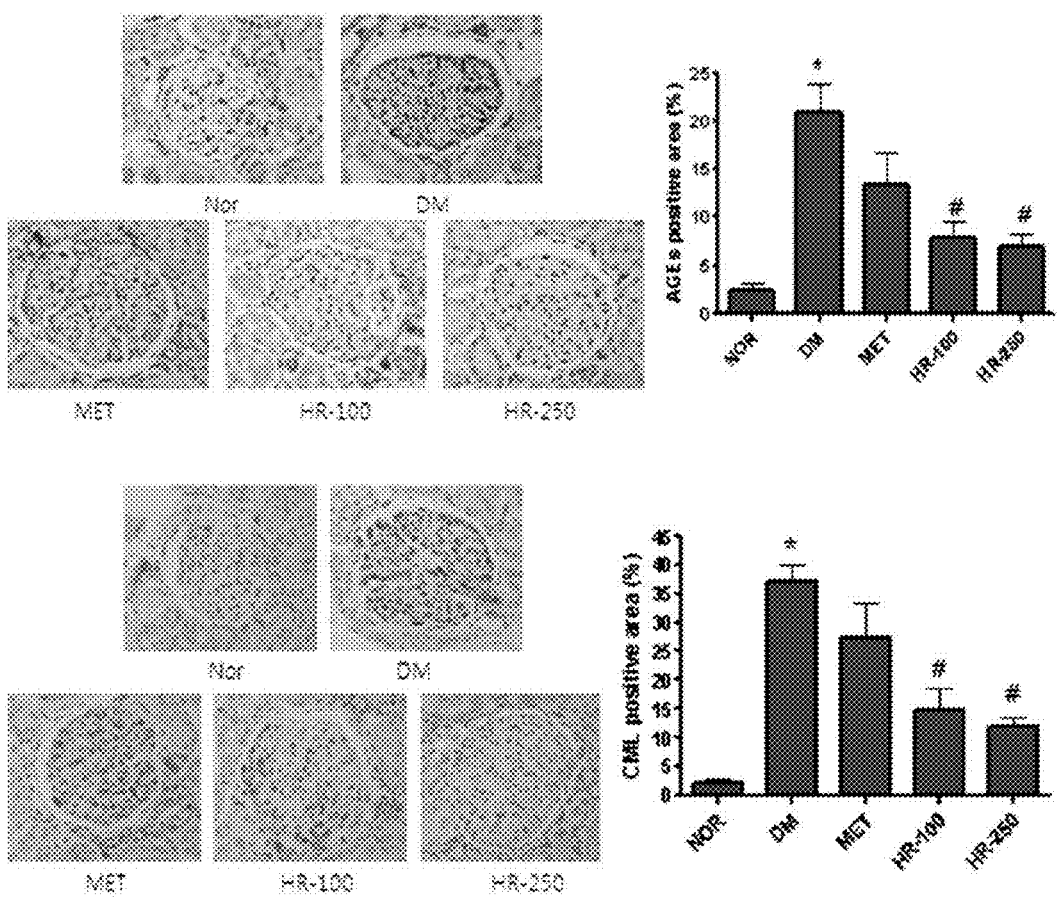
FIG. 8 is a set of photographs and graphs illustrating the effect of the extract of *Homonoia riparia* Lour. on the levels of the advanced glycation endproducts and CML in kidney of type II diabetic animal model (SDT).

As a result, as shown in FIG. 6, proteinuria and Ccr were significantly increased in the diabetic group (DM), compared with those in the normal group (NOR). Proteinuria was higher in the MET treated group (MET) than in the diabetic group (DM), but significantly lower in the group treated with the extract of *Homonoia riparia* Lour. (HR-100 or HR-250) than in the diabetic group (DM). Albuminuria was also significantly increased in the diabetic group (DM), compared with in the normal group (NOR). However, albuminuria was significantly reduced in the MET treated group (MET) or in the group treated with the extract of *Homonoia riparia* Lour. (HR-100 or HR-250), compared with in the diabetic group (DM). The similar result was confirmed by Ccr analysis (FIG. 6). As shown in FIG. 7, AGEs and CML in urine were measured. As a result, AGEs and CML were significantly increased in the diabetic group (DM), compared with in the normal group (NOR). AGEs and CML were not much reduced in the MET treated group (MET). In the meantime, in the group treated with the extract of *Homonoia riparia* Lour. (HR-100 or HR-250), AGEs and CML were significantly decreased (FIG. 7). From the results of histological staining and blotting, it was confirmed that the accumulation of AGEs and CML was significantly increased in the diabetic group (DM), compared with in the normal group (NOR). The accumulation of AGEs and CML was significantly reduced in the group treated with the extract of *Homonoia riparia* Lour. (HR-100 or HR-250) dose-dependently (FIG. 8).

<4-3-2> Analysis of Pathological Changes in Glomerulus

The kidney was extracted from the animal model during the autopsy, which was fixed in 10% neutralized formalin for overnight. After dehydration, xylene substitution was performed three times, followed by paraffin embedding. The embedded tissue block was cut into 4 μm thick sections, which were placed on the slide. To observe morphological changes, PAS (periodic acid skiff) and Masson's trichrome staining were performed. Then, the slide was observed under optical microscope.

Figure 9:
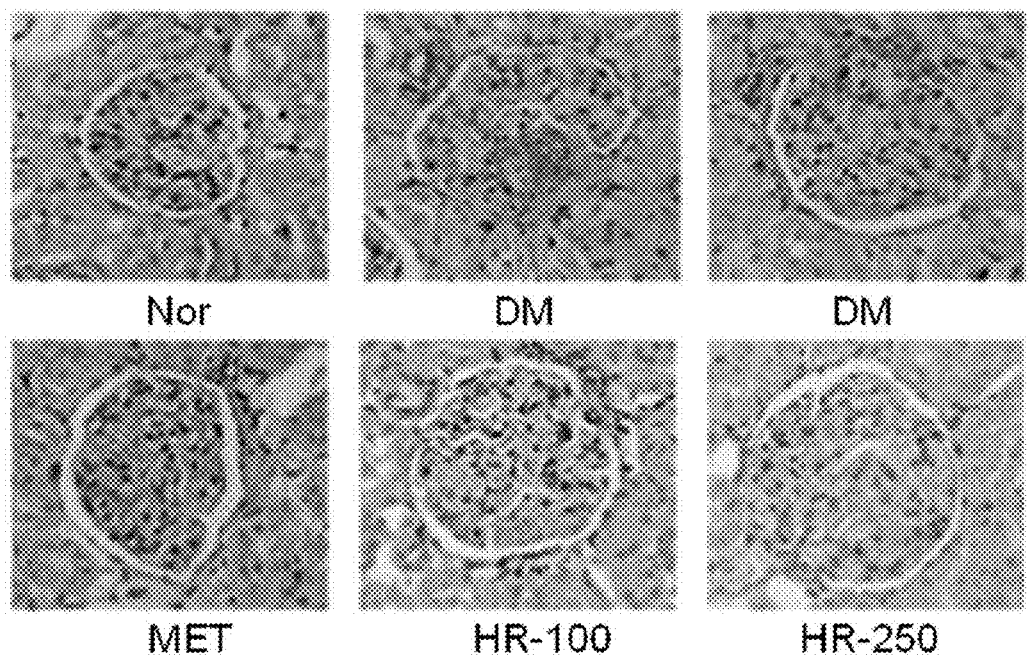
FIG. 9 is a set of photographs illustrating the effect of the extract of *Homonoia riparia* Lour. on the morphological changes caused by the accumulation of extracellular matrix in type II diabetic animal model (SDT), confirmed by PAS staining.
Figure 10:
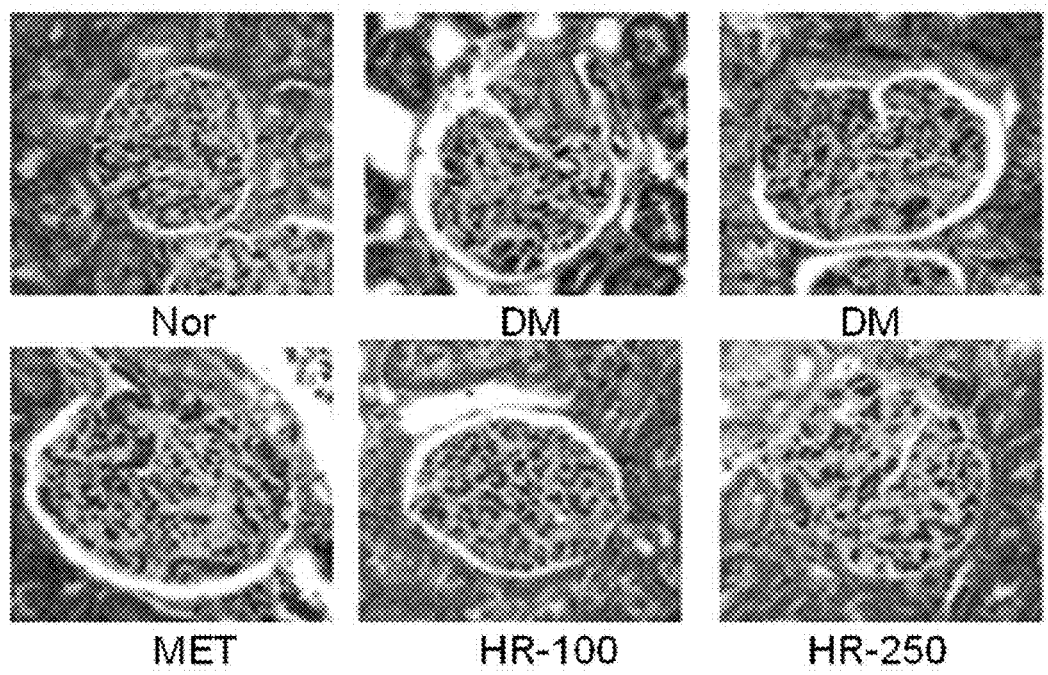
FIG. 10 is a set of photographs illustrating the effect of the extract of *Homonoia riparia* Lour. on the morphological changes caused by the accumulation of extracellular matrix in type II diabetic animal model (SDT), confirmed by Masson's Trichrome staining.

As a result, as shown in FIG. 9, glomerular basememberane hyperplasia, mesangial matrix expansion, glomerular hypertrophy, and glomerulosclerosis, caused by the accumulation of extracellular matrix, were peculiar in glomerulus of the diabetic group (DM), compared with the normal group (NOR). However, glomerular hypertrophy and mesangial matrix expansion were significantly reduced in the group treated with the extract of *Homonoia riparia* Lour. (HR-100 or HR-250) dose-dependently. Morphological changes were decreased in the MET treated group (MET) than in the diabetic group (DM), which was not so significant, though (FIG. 9). To evaluate fibrosis resulted from the deposited collagen in kidney cortex, Masson's trichrome staining was performed. As a result, collagen presenting blue in the glomerulus was bigger in the diabetic group (DM) than in the normal group (NOR). Collagen deposition in the MET treated group (MET) was not much different from that in the diabetic group (DM). However, collagen deposition in the group treated with the extract of *Homonoia riparia* Lour. (HR-100 or HR-250) was significantly reduced, compared with in the diabetic group (DM) (FIG. 10).

<4-3-3> Preventive Effect on Podocyte Loss

In the early stage of diabetes, podocyte loss occurs. To investigate the effect of the extract of *Homonoia riparia* Lour. on podocyte loss by using synaptopodin and WT-1 known as podocyte markers, the quantity of discharged podocyte in urine was measured by immunohistological staining.

As a result, podocyte loss was significantly increased in the diabetic group (DM), compared with in the normal group (NOR). In the group treated with the extract of *Homonoia riparia* Lour. (HR-100 or HR-250), the quantity of discharged podocyte was significantly reduced, indicating podocyte loss was prevented.

The Manufacturing Examples for the composition of the present invention are described hereinafter.

Manufacturing Example 1

Preparation of Pharmaceutical Formulations

<1-1> Preparation of Powders

| | |
|---|---|
| Ethanol extract of Example <1-1> | 2 g |
| Lactose | 1 g |

Powders were prepared by mixing all the above components, which were filled in airtight packs according to the conventional method for preparing powders.

<1-2> Preparation of Tablets

| | |
|---|---|
| Ethanol extract of Example <1-1> | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Normal-hexane fraction of Example <2-1> | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Normal-hexane fraction of Example <2-1> | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Normal-hexane fraction of Example <2-1> | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Foods

Foods containing the extract of *Homonoia riparia* Lour. of the present invention were prepared as follows.

<2-1> Preparation of Flour Foods 0.5~5.0 weight part of the ethanol extract of Example <1-1> was added to the flour. Flour foods such as bread, cake, cookies, crackers and noodles were prepared with the flour mixture according to the conventional method.

<2-2> Preparation of Soups and Gravies 0.1~5.0 weight part of the ethanol extract of Example <1-1> was added to soups and gravies. Health enhancing meat products, soups and gravies were prepared with this mixture by the conventional method.

<2-3> Preparation of Ground Beef

Health enhancing ground beef was prepared by mixing 10 weight part of the ethanol extract of Example <1-1> with ground beef according to the conventional method.

<2-4> Preparation of Dairy Products

5~10 weight part of the ethanol extract of Example <1-1> was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The ethanol extract of Example <1-1> was concentrated under reduced pressure, spray-dried and pulverized to obtain 60-mesh dry powders.

Sun-Sik was prepared by mixing the dry powders of the grains, seeds and the ethanol extract of Example <1-1> according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Ethanol extract of Example <1-1> (3 weight part),

*Ganoderma lucidum* (0.5 weight part),

*Rehmannia glutinosa* (0.5 weight part)

Manufacturing Example 3

Preparation of Beverages

<3-1> Preparation of Health Beverages

The ethyl acetate fraction of Example <2-2> of the present invention (2 g) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<3-2> Preparation of Vegetable Juice

Health enhancing vegetable juice was prepared by adding 5 g of the ethyl acetate fraction of Example <2-2> of the present invention to 1,000 and of tomato or carrot juice according to the conventional method.

<3-3> Preparation of Fruit Juice

Health enhancing fruit juice was prepared by adding 1 g of the ethyl acetate fraction of Example <2-2> of the present invention to 1,000 ml of apple or grape juice according to the conventional method.

Manufacturing Example 4

Preparation of Feed Additive

Feed additive containing the normal-butanol fraction of Example <2-3> as an active ingredient was prepared as follows.

<Composition of Feed Additive>

Normal-butanol fraction of Example <2-3>: 0.1~20 weight part,

Lipase: 0.001~0.01 weight part,

Calcium phosphate, tribasic: 1~20 weight part,

Vitamin E: 0.01~0.1 weight part,

Enzyme powder: 1~10 weight part,

Lactic acid bacteria: 0.1~10 weight part,

*Bacillus* culture solution: 0.01~10 weight part, and

Glucose: 20~90 weight part.

INDUSTRIAL APPLICABILITY

As explained hereinbefore, the extracts of *Homonoia riparia* Lour. or the fractions thereof of the present invention are natural substances not only effective in preventing or delaying diabetic complications but also effective in preventing aging, so that they can be effectively used as a pharmaceutical composition for the prevention and treatment of diabetic complications, for the prevention or delay of aging, and for the prevention and treatment of cancer, and for the production of a health functional food or as a functional feed additive as well.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating diabetic retinopathy comprising:
    administering a pharmaceutically effective dose of a composition comprising an extract of *Homonoia riparia* Lour, as an active ingredient, to a subject having diabetic retinopathy;
wherein the extract is prepared by extracting *Homonoia riparia* Lour. with water, $C_1$-$C_4$ lower alcohol, or a mixture thereof.

2. The method of 1, wherein the $C_1$-$C_4$ lower alcohol is ethanol or methanol.

3. The method of claim 1, wherein the $C_1$-$C_4$ lower alcohol contains 0.1%-50% of water by weight.

4. The method of claim 1, wherein the extract of *Homonoia riparia* Lour. is obtained from the leaves or twigs of *Homonoia riparia* Lour.

5. The method of claim 1, wherein treatment of the diabetic retinopathy results from inhibiting accumulation of advanced glycation endproducts in the subject.

* * * * *